(12) United States Patent
Stridfeldt et al.

(10) Patent No.: US 7,893,314 B2
(45) Date of Patent: Feb. 22, 2011

(54) BREATHABLE BACKSHEET

(75) Inventors: Chatrine Stridfeldt, Hovås (SE); Solgun Drevik, Mölnycke (SE)

(73) Assignee: SCA Hygiene Products AB, Gothenburg (SE)

( * ) Notice: Subject to any disclaimer, the term of this patent is extended or adjusted under 35 U.S.C. 154(b) by 705 days.

(21) Appl. No.: 10/565,630

(22) PCT Filed: Oct. 29, 2004

(86) PCT No.: PCT/SE2004/001570
§ 371 (c)(1),
(2), (4) Date: Jan. 24, 2006

(87) PCT Pub. No.: WO2005/041832
PCT Pub. Date: May 12, 2005

(65) Prior Publication Data
US 2006/0286353 A1  Dec. 21, 2006

(30) Foreign Application Priority Data
Oct. 31, 2003  (SE) .................................. 0302867

(51) Int. Cl.
*A61F 13/15* (2006.01)
*A61F 13/20* (2006.01)
(52) U.S. Cl. ................. 604/380; 604/367; 604/382
(58) Field of Classification Search .......... 604/367, 604/379–380, 385.01
See application file for complete search history.

(56) References Cited

U.S. PATENT DOCUMENTS

| 3,881,489 A | * | 5/1975 | Hartwell ................... 604/369 |
| 4,341,216 A | * | 7/1982 | Obenour ................... 604/370 |
| 4,681,793 A | * | 7/1987 | Linman et al. ............ 428/138 |
| 5,928,209 A | * | 7/1999 | Bodford et al. ........... 604/370 |
| 6,232,521 B1 | * | 5/2001 | Bewick-Sonntag et al. .. 604/378 |
| 2002/0019187 A1 | | 2/2002 | Carroll et al. |
| 2005/0065490 A1 | * | 3/2005 | Shimoe et al. ............ 604/367 |

FOREIGN PATENT DOCUMENTS

| EP | 1040799 | 10/2000 |
| EP | 1040800 | 10/2000 |

(Continued)

OTHER PUBLICATIONS

JP Office Action dated Jun. 1, 2010 in JP 2006-537937.

*Primary Examiner*—Michele Kidwell
(74) *Attorney, Agent, or Firm*—Young & Thompson

(57) ABSTRACT

A breathable backsheet (1) includes a water vapor permeable first layer (2) and a water vapor permeable second layer (3) for an absorbent article (4), where the backsheet (1) is water vapor permeable in a Z-direction. The backsheet (1) includes a condensation zone (7) between the two layers (2, 3). The first layer (2) is adapted to allow a first amount $m_1$ of mass flow water vapor to pass the first layer (2) in the Z-direction, wherein the second layer (3) is adapted to allow a second amount $m_2$ of mass flow water vapor to pass the second layer (3) in the Z-direction. The condensation zone (7) is adapted to temporary condense and shore an amount $t \cdot m_c$ of water vapor such that no formation of condensed of water vapor will occur on the outside (6, 11) of the backsheet (1).

4 Claims, 6 Drawing Sheets

FOREIGN PATENT DOCUMENTS

| | | |
|---|---|---|
| EP | 1040807 | 10/2000 |
| JP | 2003025471 | 1/2003 |
| WO | WO 97/24096 A1 | 7/1997 |
| WO | 9802610 | 1/1998 |
| WO | 0059425 | 10/2000 |

* cited by examiner

BREATHABLE BACKSHEET

TECHNICAL FIELD

The invention refers to a breathable backsheet for an absorbent article. The backsheet comprises a water vapour permeable first layer and a water vapour permeable second layer. The absorbent article comprises an absorbent body adjacent the first layer and is adapted for use of a user such that the absorbent body during use faces towards the user and such that an outside of the backsheet faces away from the user during use. The backsheet is water vapour permeable in a direction from the absorbent body to the outside of the backsheet, in a Z-direction.

BACKGROUND ART

Absorbent articles such as diapers, sanitary napkins and the like, are used to collect bodily fluids from a person using the article during a fluid discharge. The absorbent articles are equipped with a liquid-impermeable backsheet on the outside of the article, i.e. that side of the article that faces away from a user during use, and an absorbent body placed between the liquid-impermeable backsheet and the user's body. The absorbent body is arranged to absorb the bodily discharge and the liquid-impermeable backsheet is intended to hinder the absorbed liquid in the absorbent body from leaking to the outside of the article.

It is also known to use so called breathable backsheets for absorbent articles, i.e. water vapour permeable backsheets that allows water vapour to be transported from within the absorbent article to the outside of the absorbent article via the backsheet, i.e. in the Z-direction. The breathable backsheets are intended to diminish the amount of water vapour within the article, since such water vapour may cause a too humid microclimate adjacent the skin of the user. Such humid microclimate may cause irritation on the user's skin.

One problem with breathable backsheets is the formation of condensed water vapour on the outside of the article, i.e. on the outside of the backsheet. The condensed water gives a wet and uncomfortable feel for the user. Furthermore, the condensed water may be transferred to the clothing of the user, which may develop into an unpleasant wet spot visible on the user's clothing.

A number of solutions are present in the background art, for example the use of an absorbent body on the outside of the backsheet, where the absorbent body is intended to absorb the condensed water vapour. A problem with such a solution is that the backsheet and the absorbent body become thick and uncomfortable for the user. Another problem is that the absorbent body cannot hold the liquid during high pressure, e.g. when the user is sitting down, which may cause the release of liquid from the absorbent body such that an indiscreet wet spot may appear on the user's clothing.

U.S. Pat. No. 5,814,035 shows a breathable backsheet arrangement comprising two breathable layers. The arrangement is intended to minimise the formation of condense on the outside of the backsheet. Between the layers are positioned desiccant particles adapted for drying the moist air passing through the backsheet by absorbing the water vapour in the zone between the two layers. According to U.S. Pat. No. 5,814,035, suitable desiccant particles are made from calcium chloride, super absorbent materials, silica gel or the like.

One disadvantage with the arrangement according to U.S. Pat. No. 5,814,035 is that the desiccant particles absorb water vapour whereby the backsheet arrangement increases in weight and thickness. For example, the absorbed water vapour causes the super absorbents to swell and become thick, which gives a less flexible backsheet which makes the absorbent article less comfortable for a user. Furthermore, the desiccant materials have a maximum power of absorption. When the maximum limit is reached, the desiccant particles cannot absorb any more water vapour which leads to an increased water vapour transport to the outside of the backsheet with a formation of condensed water on the outside of the backsheet as a consequence.

There is thus still a need for a breathable backsheet adapted for an absorbent article with a minimised or no formation of condensed water on the outside of the backsheet during use.

DISCLOSURE OF INVENTION

It is an object of the present invention to rectify the above-discussed problems and to present a backsheet for an absorbent article, such as a diaper, incontinence article, etc., with an improved water handling capability such that there will be a minimised or no formation of condensed water on the outside of the backsheet during use of the absorbent article.

The invention refers to a breathable backsheet comprising a water vapour permeable first layer and a water vapour permeable second layer for an absorbent article comprising an absorbent body adjacent the first layer. The absorbent article is adapted for use of a user such that the absorbent body during use faces towards the user and such that an outside of the backsheet faces away from the user. The backsheet is water vapour permeable in a direction from the absorbent body to the outside of the backsheet, in a Z-direction. Both the first and second layer is liquid impermeable.

The invention is characterised in that the backsheet comprises a condensation zone between the two layers. The first layer is adapted to allow a first amount $\dot{m}_1$ of mass flow water vapour to pass the first layer in the Z-direction, and the second layer is adapted to allow a second amount $\dot{m}_2$ of mass flow water vapour to pass the second layer in the Z-direction, where $\dot{m}_2$ is less than or equal to $\dot{m}_1$. The condensation zone is adapted to temporary condense and store an amount $t \cdot \dot{m}_c$ of water vapour where $\dot{m}_c$ is the difference between $\dot{m}_1$ and $\dot{m}_2$, and where t is the time period during which the condensed water vapour $\dot{m}_c$ is stored, and where $\dot{m}_2$ is less than a maximum amount $\dot{m}_x$ of mass flow water vapour allowed to pass the second layer without forming any condense of water vapour on the outside of the backsheet.

The benefit of the present invention is that there will be a minimum or no formation of condenses on the outside of the backsheet when the absorbent article is in use. This is advantageous for a user who will feel no discomfort due to a wet outside of an absorbent article.

The first layer is adapted to allow the first amount $\dot{m}_1$ of mass flow water vapour to be maximum 10000 $g/(m^2 \cdot 24$ hours).

The second layer is adapted to the second amount $\dot{m}_2$ of mass flow water vapour to be maximum 2700 $g/(m^2 \cdot 24$ hours).

The flow rates are given when the outside air has a relative humidity of about 90% and a temperature of about 23° C. The testing procedure used is ASTM-398 using Lyssy equipment.

In one embodiment of the invention, the backsheet comprises a hydrophobic distance element placed in the condensation zone, arranged to condense water vapour within the condensation zone.

In one embodiment, the distance element is made from a number of hydrophobic particles.

In another embodiment, the distance element is made from a three dimensional hydrophobic distance layer comprising raised portions and depressions. The raised portions on one side of the distance layer are in contact with the first layer and the raised portions on the other side of the distance layer are in contact with the second layer. The depressions form spaces between the first layer and the second layer. The spaces constitute the condensation zone In yet a further embodiment, the first layer and/or the second layer has a three dimensional form with raised portions and depressions therebetween, such that the raised portions of the first and second layers are in contact in several points, and where the condensation zone is created in the space between the depressions of the first and second layer. The raised portions may form hydrophobic distance elements for supporting the condensation zone.

The condensation zone is an open volume between the first layer and the second layer, where the minimum distance between the first layer and the second layer is 0.1 mm. The condensation zone may be created by any of the above stated embodiments, either alone or in combination.

The above stated features of the backsheet are valid in an environment where the outside of the backsheet is uncovered and exposed to a room temperature of about 20° C. Room temperature refers to the prevailing temperature in the environment on the outside of the diaper. Different mass flow rates may be allowed during different room temperature conditions.

The first layer may be made from a hydrophobic material such as; a micro-porous polyolefin based film, polyethylene, polypropylene, or a polyolefin non-woven, or a hydrophobic tissue, or a plastic film with a number of apertures. The first layer may also be made from any of the above materials with a latex coating.

The second layer may be made from the same material as the first layer, but the second layer may have a different composition than the first material.

The first and second layer shall be water impervious and water vapour pervious. Each of the layers thus has a number of aperture/pores that allows the above stated flow rates for water vapour at the same time as liquid water is blocked. For example, the apertures in the first layer may preferably be larger than the apertures in the second layer in order to allow the different flow rates of water vapour.

BRIEF DESCRIPTION OF DRAWINGS

The invention will below be discussed in greater details in connection with a number of figures, where.

MODES FOR CARRYING OUT THE INVENTION

Figure 1:
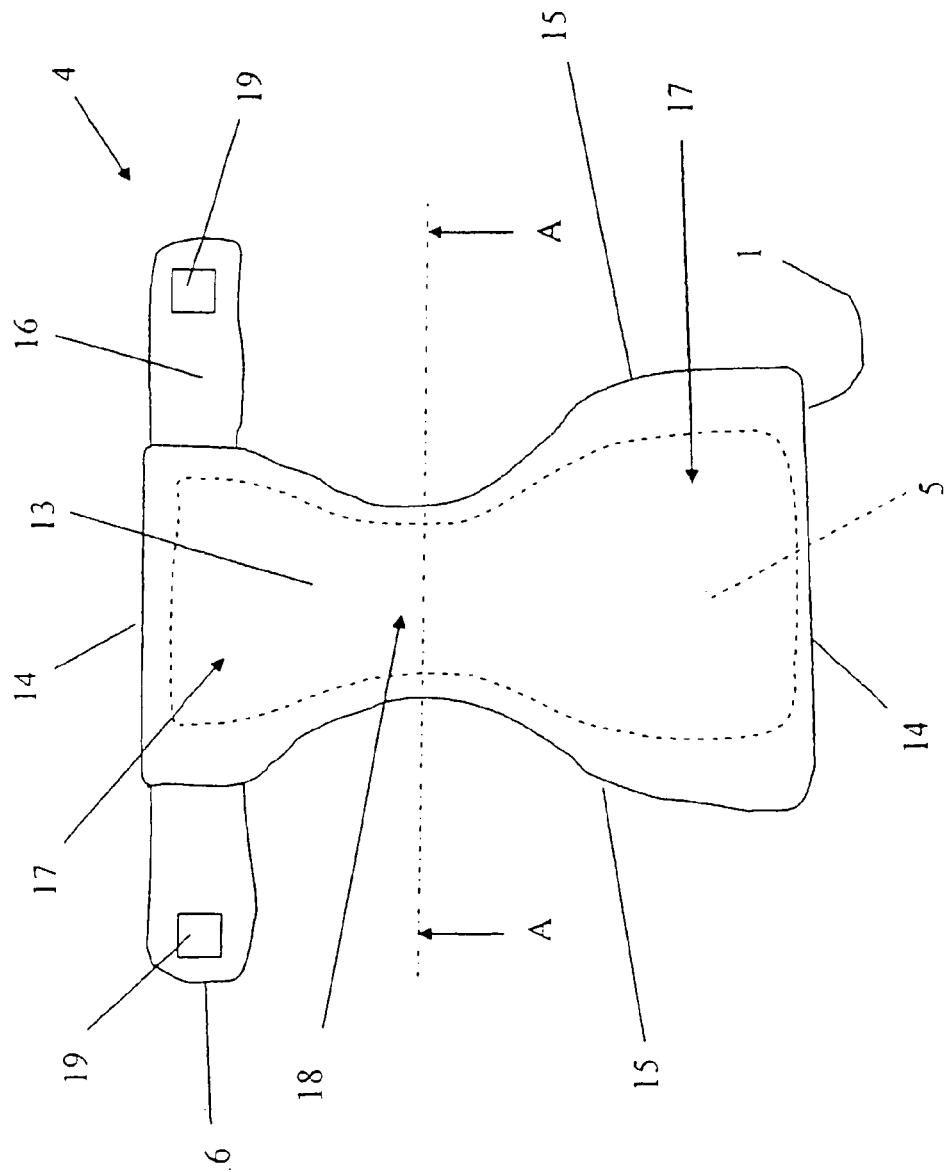
FIG. 1 schematically shows a perspective view of an absorbent article.

FIG. 1 schematically shows a perspective view of an absorbent article 4 comprising a topsheet 13, a breathable backsheet 1 and an absorbent body therebetween. The absorbent article 4 extends in a longitudinal direction between two short sides 14 and in a lateral direction between two long sides 15. The absorbent article is in the longitudinal direction divided into two end sections 17 end a therebetween extending central section 18. The absorbent article 4 comprises two flaps 16 extending in the lateral direction and attached on the long sides 16 at a position close to one of the short sides 14, i.e. at one of the end sections 17. When the article is in use, the absorbent article 4 is intended to be folded around the genital area of the user such that; the central section 18 is placed against the genital area; one of the end sections 17 of the article is placed over the lower abdomen; and such that the other end section 17 of the article is placed over the lower back of the user. The flaps 16 are intended to be folded over the hips of the user and then via fastening means 19 fastened to the end section 17 opposite the end section 17 on which the flaps 16 are fastened, thereby forming side portions of the absorbent article 4.

Figure 2:
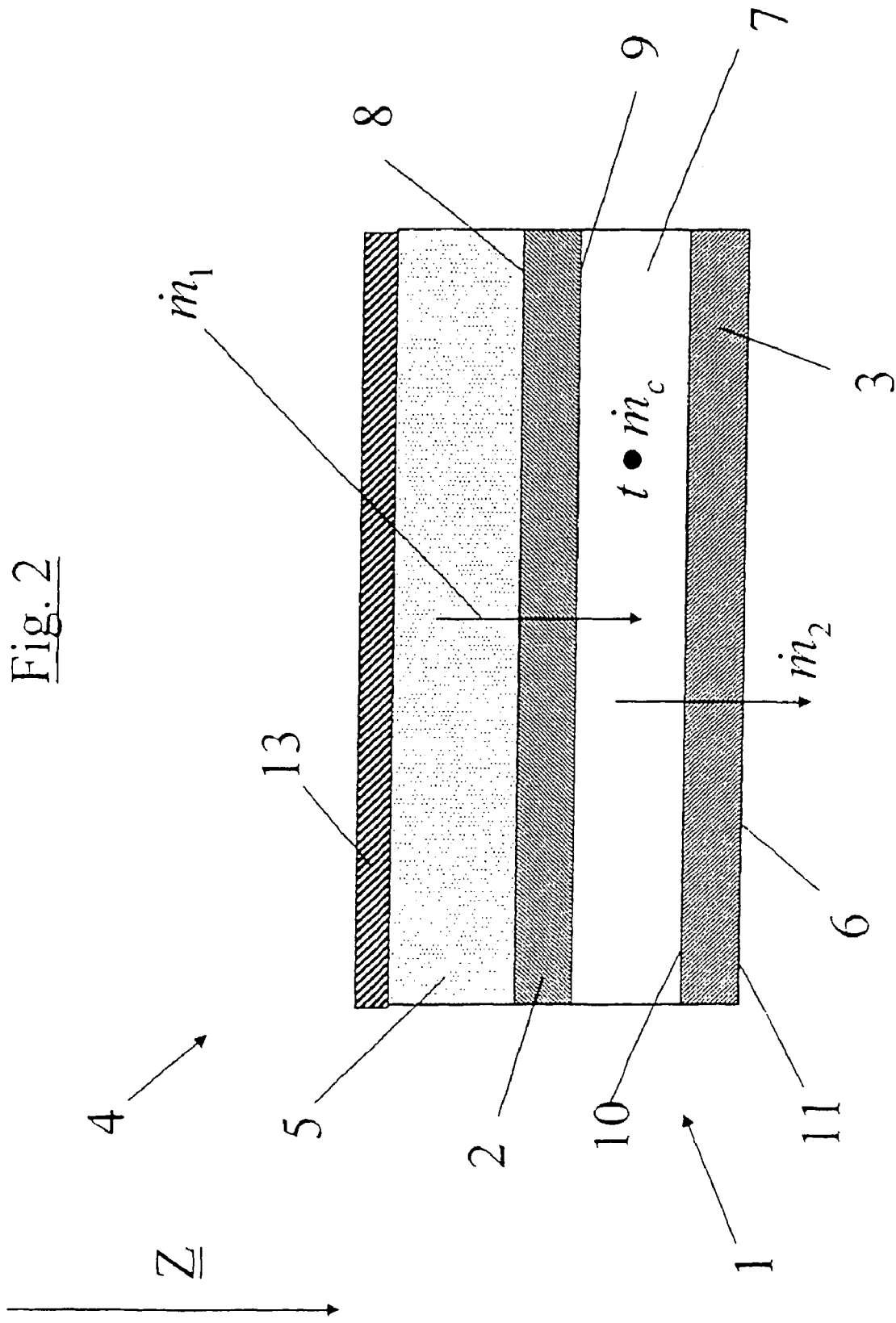
FIG. 2 schematically shows a cross-section view taken in the cross-section A-A in FIG. 1, according to a first embodiment of the present invention.

FIG. 2 schematically shows a cross-section view in the cross-section A-A in FIG. 1 of a first embodiment of the invention. The backsheet 1 is water vapour permeable, but is also impermeable to liquid water. The absorbent article 4 is arranged such that, during use, the topsheet 13 is placed towards a user and an outside 6 of the backsheet 4 faces away from the user. The backsheet 1 is water vapour permeable in the direction from the user to the outside 6 of the backsheet 1 in a Z-direction, i.e. in the direction from the topsheet 13 to the backsheet 1. The Z-direction is shown in FIG. 2 as an arrow pointing in the flow direction and is marked with an underlined letter Z.

The breathable backsheet 1 comprises a water vapour permeable first layer 2 and a water vapour permeable second layer 3. The absorbent body 5 is placed adjacent the first layer 2 and the topsheet 13. The backsheet 1 further comprises a condensation zone 7 between the two layers 2, 3, wherein the first layer 2 is adapted to allow a first amount $\dot{m}_1$ of mass flow water vapour to pass the first layer 2 in the Z-direction. The second layer 3 is adapted to allow a second amount $\dot{m}_2$ of mass flow water vapour to pass the second layer 3 in the Z-direction. According to the invention $\dot{m}_2$ is less than or equal to $\dot{m}_1$, wherein the condensation zone is adapted to temporary condense and store an amount $t \cdot \dot{m}_c$ of water vapour where $\dot{m}_c$ is the difference between $\dot{m}_1$ and $\dot{m}_2$, and where t is the time period during which the condensed water vapour $\dot{m}_c$ is stored, and where $\dot{m}_2$ is less than a maximum amount $\dot{m}_x$ of mass flow water vapour allowed to pass the second layer 3 without forming any condense of water vapour on the outside 6 of the backsheet 1.

The condensation zone 7 is not intended to absorb water vapour, but to accumulate and store an excess amount of water vapour during a predetermined time period.

The second layer 3 is adapted such that a maximum rate of water vapour $\dot{m}_x$ is allowed to pass the second layer 3 in the Z-direction. This limit is set by the conditions present on the outside 6 of the backsheet 1 and in close vicinity to the outside 6 of the backsheet 1. The conditions determine at what rate the transport of water vapour causes the formation of water condense on the outside 6 of the backsheet 1.

In order to facilitate the understanding of the invention an example will now be presented:

In a normal indoor environment at a temperature of about 20° C. where the outside 6 of the backsheet 1 is uncovered, the outside 6 of the backsheet 1 has essentially the same temperature as the surrounding air, i.e. the room temperature. Furthermore, the climate close to the outside 6 of the backsheet 1 is essentially the same as in the room, e.g. regarding the moisture content etc.

Inside the absorbent article 4, a certain climate prevails after a urinal discharge. The temperature of the urine is at a normal body temperature, i.e. essentially 37° C. The urine is absorbed by the absorbent body 5 where the temperature more or less is preserved at about 33-35° C. for a certain time period, and then slowly decreases to about 26-31° C. The temperature is more or less preserved since the absorbent body 5 is arranged close to the body of the user; and the body radiates heat into the wet absorbent body 5; and the absorbent body 5 acts as an insulator between the outside conditions and the body. The thickness of the absorbent article is of importance regarding the preservation of heat and the rate of which the temperature decreases. Thicker articles isolate better than do thinner articles, why a thinner article has a part of the absorbent body close to the backsheet that is warmer than the corresponding part of a thicker article. The skin temperature of a human being is about 33-35° C. and the skin/body therefore heats up the water vapour close to the users body to approximately the skin temperature, why the absorbent body 5 thus contains saturated water vapour of at least the same temperature, i.e. at about 33-35° C. It is essential to transport this water vapour away from the absorbent article since the moisture may cause skin irritation to the user. According to the invention, the saturated water vapour is transported in the Z-direction passing the first layer 2 at a first rate $\dot{m}_1$.

The first layer 2 has an inside surface 8 towards the absorbent body and an outside 9 forming a wall in the condensation zone 7. The outside 9 of the first layer 2 transfers heat to the outside of the absorbent article, via the condensation zone 7 and the second layer 4, why the temperature drops accordingly in the vicinity of the outside 9 of the first layer 2. On the other hand, on the inside surface 8 of the first layer 2 the conditions in the absorbent body 5 prevails. The temperature on the outside 9 of the first layer 2 has thus a lower temperature than does the inside surface 8 of the first layer 2.

Before any discharge has occurred, the conditions prevailing in the condensation zone 7 is more or less the same as on the outside 6 of the absorbent article, i.e. 20° C. as in the mom according to the example above.

At 20° C. the moisture content may vary as $0 < \phi < 1$ where $\phi$ is the relative humidity, i.e. the quota between the partial pressure $P_1$ of vapour at a given temperature and the partial pressure $P_s$ of saturated vapour at the given temperature. When $\phi$ is equal to 1 the air is saturated with water vapour. The same goes for air at a higher temperature (or lower), for example at 37° C., but saturated air at the higher temperature holds a larger amount of water vapour.

It is known that warm air can contain more water vapour, i.e. a higher partial pressure water vapour, than colder air. When warm saturated air is chilled to a lower temperature, the colder air may only hold a part of the original amount of vapour. The excess amount of vapour is condensed and will thus appear as liquid water.

In prior art it is a well known problem with condensed air on the outside of the absorbent article due to the temperature difference between the outside and the inside of the absorbent article, as described above.

In the present invention, the water vapour $\dot{m}_1$ that passes through the first layer 2 has a temperature $T_1$ which is higher than the temperature $T_{cz}$ in the condensation zone. Some of the water vapour will therefore condense on the outside 9 of the first layer 2. However, the condensed water will not appear on the outside 6 of the backsheet 1, but will be enclosed within the condensation zone 7.

Furthermore, the second layer 3 has an inside surface 10 forming a second wall in the condensation zone 7 and an outside 11 that in this embodiment is the outside 6 of the backsheet 1. The condensation zone 7 is a space between the outside 9 of the first layer 2 and the inside surface 10 of the second layer. The space between the two layers 2, 3 has minimum distance of 0.1 mm. The minimum distance may be kept by means of a number of distance elements in the form of, for example hydrophobic particles, or a hydrophobic net structure, or strips of a hydrophobic material, or a three dimensional hydrophobic net structure. Furthermore, the first layer 2 and/or the second layer 3 may be embossed or otherwise formed in a three dimensional manner such that some parts of the two layers 2, 3 are in connection with each other forming distance elements, and some parts of the two layers 2, 3 are separated from each other such that the space forming the condensation zone 7 is created between the layers 2, 3. Different embodiments of suitable distance elements will below be further explained in connection with FIGS. 3-6.

The space forming the condensation zone 7, may extend over the complete surface of the first and second layers 2, 3 as shown in FIG. 2, or may be in the form of a number of spaces spread out over the extension of the first and second layers 2, 3 (se FIGS. 3-6).

Before any urinal discharge, the condensation zone 7 is essentially filled with air with the same specifications as the outside air. After the discharge, the condensation zone 7 is, via the first layer 2, gradually filled with water vapour from the absorbent body 5. When entering the condensation zone, the water vapour is partly condensed. At the same time as the water vapour enters the condensation zone 7, the temperature increases somewhat in the condensation zone 7. As mentioned before air of a higher temperature may hold more water vapour than can colder air. The second layer 3 is very thin and conducts heat well such that the inside surface 10 of the second layer 3 is cooled by the outer temperature in such a way that the inside surface 10 of the second layer 3 has a temperature about the same as the room temperature. The inside surface 10 of the second layer 3 has thus a temperature equal to or lesser than the air in the condensation zone 7. Hence, the temperature in the condensation zone 7 rises according to the above, but the temperature $T_{is}$ on the inside surface 10 of the second layer 3 is either equal to (initially) or less (after discharge) than the air temperature $T_{cs}$ in the condensation zone 7. As a consequence, the water vapour in the condensation zone 7 will condense not only on the outside 9 of the first layer 2 but also on the inside surface 10 of the second layer 3 as well.

As a consequence of the above, the condensation zone 7 will directly after a discharge start to accumulate condensed water. However, it is not desirable to store condensed water in the condensation zone 7. According to the invention the condensation zone 7 shall only buffer the condensed water before further transport to the outside of the absorbent article 4. Therefore, the condensation zone 7 shall not comprise means for absorbing and storing water.

According to the invention the second layer 3 is vapour-permeable as the first layer 2, but allows a different flow rate of water vapour, i.e. allows a second amount $\dot{m}_2$ of mass flow water vapour to pass the second layer 3 in the Z-direction.

According to the invention $\dot{m}_2$ is less than or equal to $\dot{m}_1$ dependent on the situation in the condensation zone 7. If there is no accumulation of condensed water within the condensation zone 7, $\dot{m}_2$ may be equal to $\dot{m}_1$. However, during the main part of the time period after the discharge $\dot{m}_2$ is less than $\dot{m}_1$ such that there will be no formation of condensed water on the outside 11 of the second layer 3.

Outside the absorbent article, i.e. on the outside 6 of the backsheet 1 (i.e. on the outside 11 of the second layer 3), the air may have different properties dependent on where the user is located. The user may be outdoors, or indoors, or in a hot environment where $\phi$ is somewhere in the range of 0 to 1, or in a cold environment where $\phi$ is somewhere in the range of 0 to 1. It would be impossible to draw examples of the invention in view of all the above possible environmental conditions. However, the driving force for the transport of the water vapour from the inside of the absorbent article (absorbent body 5) to the outside 6 of the absorbent article 4 is both in the form of a heat gradient and/or a water vapour gradient (i.e. the difference in partial pressure of water vapour) between different sides of the above mentioned first and second layers 2, 3.

The invention has been described in view of normal indoor conditions where the temperature is 20° C. and where $\phi$ is somewhere in the range of 0 to 1, but the person skilled in the art may adapt the breathable backsheet 1 according to conditions prevailing at a certain location.

If $\phi$ is equal to or close to 0 for the air outside the article, the second layer 3 may be arranged to allow $\dot{m}_2$ to be higher than if $\phi$ is equal to or close to 1. This is due to the fact that the unsaturated air at $\phi$ equal to or close to 0 absorbs a large part of the saturated and warmer air transported from the condensation zone 7 to the outside 6 of the backsheet 1, before the air close to the outside 6 of the backsheet 1 is saturated. However, the saturated air close to the outside 6 of the backsheet 1 will also be dispersed into the air in the room such that new unsaturated air is fed to the volume close to the outside 6. The new unsaturated air may further absorb more water vapour from the condensation zone 7, why essentially no condensation will appear on the outside 6 of the backsheet 1.

In the case where $\phi$ is equal to or close to 1 for the outside temperature, the second layer 3 may on the contrary be arranged to allow a lesser amount of $\dot{m}_2$ to pass the second layer 3, since the essentially saturated outside air may not absorb any more water vapour The above-described examples are two extreme situations which nearly never will occur, why a manufacturer of a breathable backsheet looks at a normal environment for the use of an absorbent article. Such normal environment may be chosen to be the indoor conditions of a temperature of about 18° C. to 22° C. and where $\phi$ is equal to about 0.3-0.6.

The first layer 2 is arranged to allow the first amount $\dot{m}_1$ of mass flow water vapour to pass the first layer 2 in the Z-direction dependent on the features of the second layer 3. The first layer may be arranged to allow $\dot{m}_1$ to be higher than $\dot{m}_2$ since the condensation zone 7 may temporary store any excess of water vapour as condensed water.

One important feature of the invention is that the backsheet 1 is breathable without forming any condense on the outside 6 of the backsheet 1 at a given condition of the outside air regarding the temperature and partial pressure of vapour in the outside air. Furthermore, the backsheet 1 is not intended to hold any condensed water within the condensation zone 7, but the condensed water within the condensed zone 7 will by time evaporate again and will then be transported to the outside 6 of the backsheet 1. The evaporation of the condensed water within the condensation zone 7 will appear after a certain time after the discharge, dependent on the current transport of water vapour to the condensation zone 7 as well as the current transport of water vapour from the condensation zone 7 to the outside 11 of the second layer 3. The air in the condensation zone 7 strives towards always being saturated (this is known in the literature) why the condensed water within the condensation zone 7 will evaporate when the transport from the inside of the absorbent article (i.e. from the absorbent body 5) slows down or ceases and when the transport from the condensation zone 7 to the outside 6 of the backsheet 1 continues due to temperature difference and/or the difference in partial pressure of water vapour.

As mentioned before, the condensation zone 7 is adapted to temporary condense and store an amount $t \cdot \dot{m}_c$ of water vapour where $\dot{m}_c$ is the difference between $\dot{m}_1$ and $\dot{m}_2$, and where t is the time period during which the condensed water vapour $\dot{m}_c$ is stored, and where $\dot{m}_2$ is less than a maximum amount $\dot{m}_x$ of mass flow water vapour allowed to pass the second layer without forming any condense of water vapour on the outside of the backsheet.

In the above t may be regarded as one time period in a series of time periods during which a different amount of water vapour is condensed and accumulated, but in practise the process should be regarded as a continuous process.

The invention may thus be regarded in view of the following:

$$t_{tot} \cdot \dot{m}_{totc} = t_{tot} \cdot \dot{m}_1 = t_{ttot} \cdot \dot{m}_2 + t_n \cdot \dot{m}_{cz,n} = \sum_{0}^{n} t_n \cdot \dot{m}_{cz,n}$$

$t_{tot}$=the total time from the discharge to the end of the process $\dot{m}_{tot}$=the total amount of mass flow water vapour transported from the inside of the absorbent article.

$\dot{m}_{cx,n}$=the amount of mass flow water vapour condensed within the condensation zone during each time period n.

n=the number of time periods according to above

The amount $\dot{m}$ of mass flow water vapour may be expressed as kg/s or mole/s or as a flux $kg/sm^2$ or $mole/sm^2$. The amount $\dot{m}$ of mass flow water vapour may also be expressed as a partial pressure P of water vapour in an air stream of a certain velocity m/s. It is just a matter of converting according to known physical laws, e.g. the ideal gas law (since the prevailing pressures and temperatures are fairly moderate the ideal gas law applies satisfactory).

The conditions within the absorbent article may be approximated as being air of 37° C. at atmospheric pressure and saturated with water vapour during a time period close to the discharge, after which the temperature slowly decreases. It is possible to use a Mollier diagram in order to find the water vapour content or partial pressure. The Mollier diagram may also be used to find the dew-point, i.e. the conditions where water vapour condenses at different temperature, which occurs when $\phi$ is equal to 1 at the given temperature.

Figure 3:
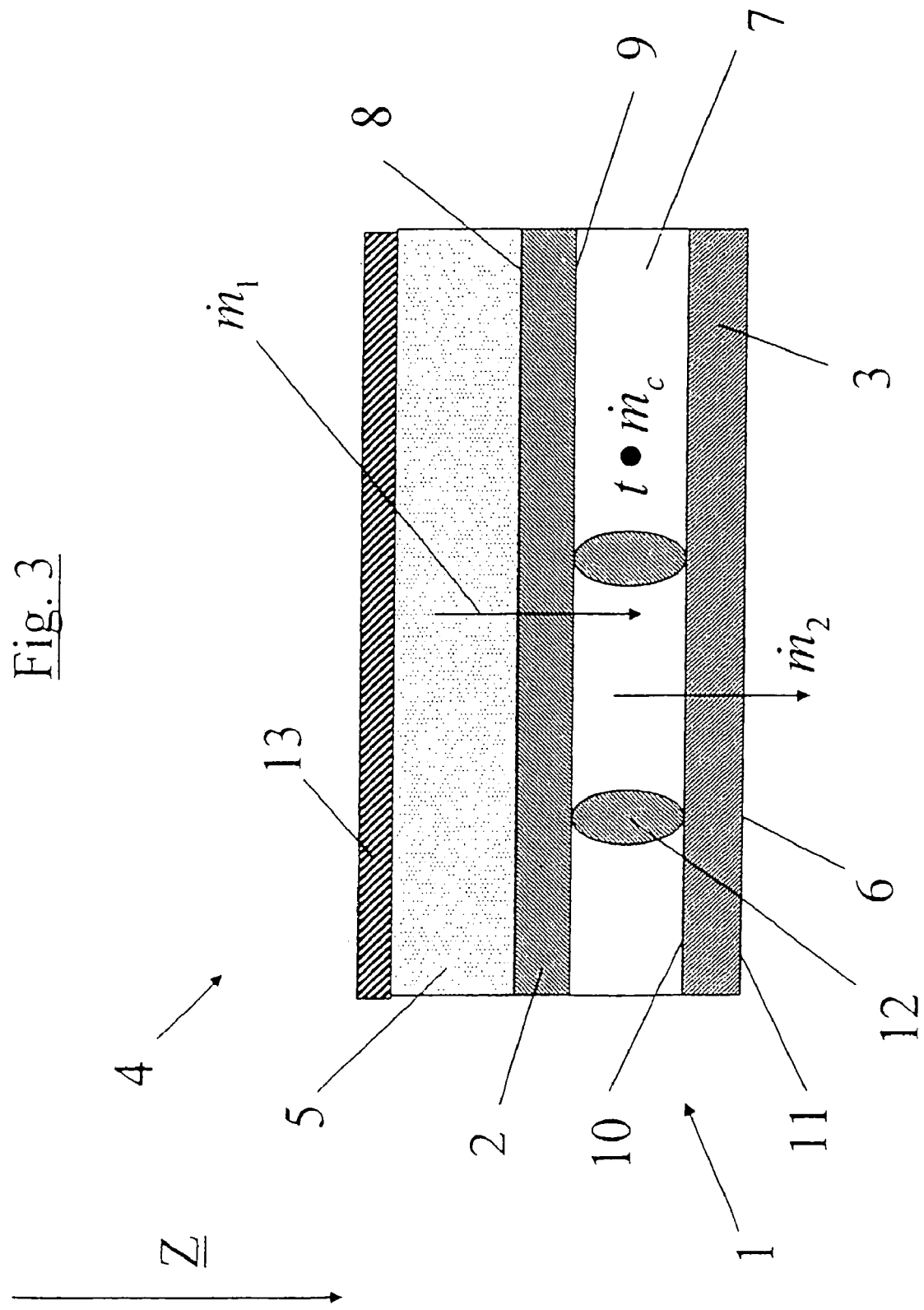
FIG. 3 schematically shows a cross-section view taken in the cross-section A-A in FIG. 1, according to a second embodiment of the present invention.

FIG. 3 schematically shows a cross-section view of the cross-section A-A in FIG. 1, according to a second embodiment of the invention. The condensation zone comprises hydrophobic particles 12 for increasing the total amount of surface accessible for condensation. The hydrophobic particles 12 shall not absorb any water vapour or condensed water, but shall only serve as a condensation means. The particles 12 also serve as distance elements between the first layer 2 and the second layer 3. The hydrophobic particles 12 may be made from any known material that is hydrophobic, i.e. which does not absorb water vapour or water. For example; any hydrophobic polymer such as, polypropylene, polyethylene, poly-lactic-acid polymer, Nylon, hydrophobic fibers, hydrophobic foam; or any hydrophobic non dissolvable inert structure.

Figure 4:
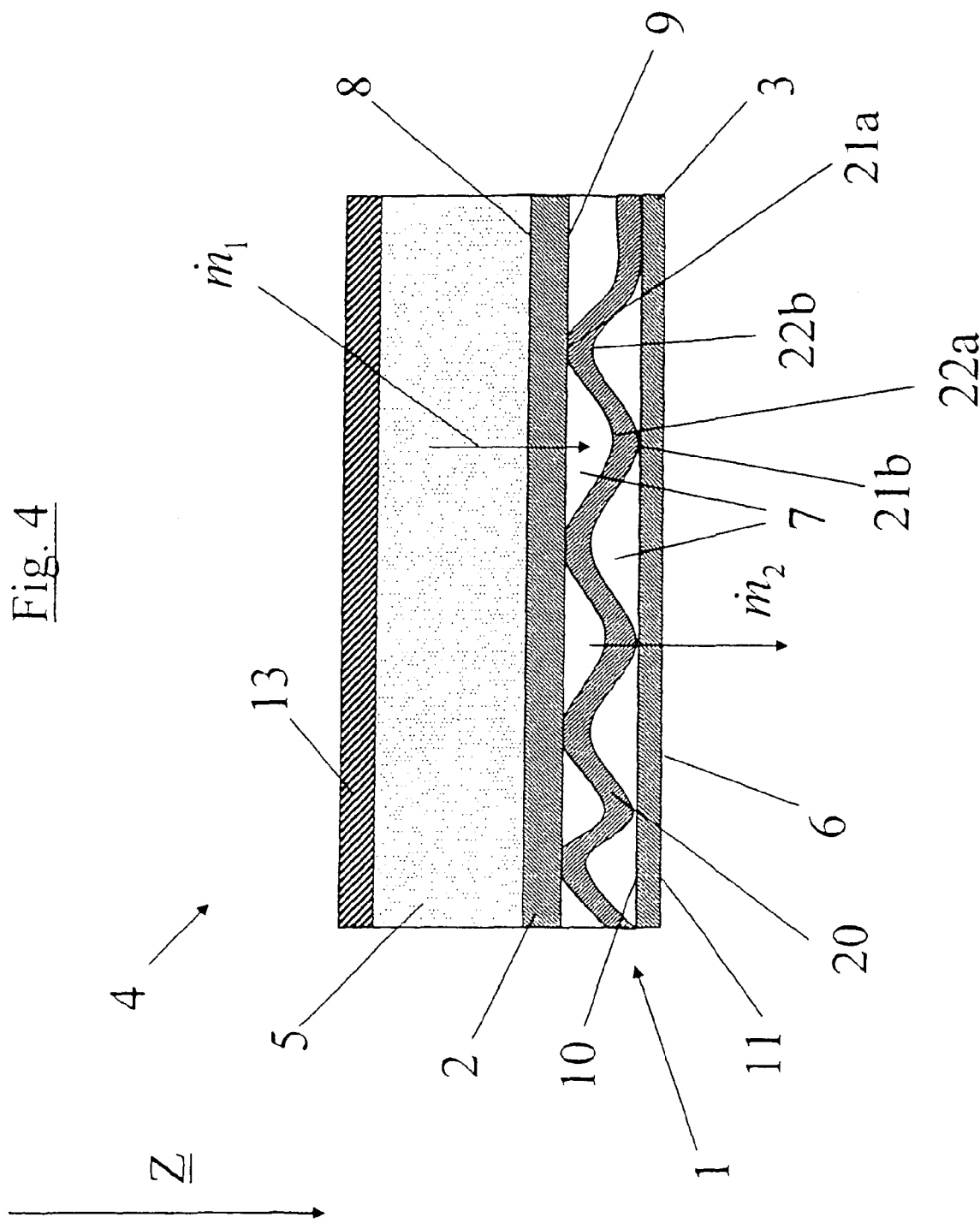
FIG. 4 schematically shows a cross-section view taken in the cross-section A-A in FIG. 1, according to a third embodiment of the present invention.

FIG. 4 schematically shows a cross-section view in the cross-section A-A in FIG. 1, according to a third embodiment of the present invention. The condensation zone comprises a three dimensional hydrophobic distance layer 20 for increasing the total amount of surface accessible for condensation. The hydrophobic distance layer 20 shall not absorb any water vapour or condensed water, but shall only serve as a condensation means. The distance layer 20 also serve as a hydrophobic distance element between the first layer 2 and the second layer 3. The three dimensional hydrophobic distance layer 20 is preferably in the form of a three dimensional net. The three dimensional distance layer 20 is water permeable. The three dimensional distance layer has a topographic feature with raised portions 21a and depressions 22a on a first side of the distance layer 20 and corresponding depressions 22b and raised portions 21b on second side of the distance layer 20. The raised portions 21a on the first side of the distance layer 20 are in contact with the first layer 2, and the raised portions 21b on the second side of the distance layer 20 are in contact with the second layer. The raised portions create a distance between the first layer 2 and the second layer 3 such that the space between the depressions 22a, 22b and the layers 2, 3 create the condensation zone 7. The distance layer 20 may be manufactured by any known production method, for example embossing. The distance layer 20 may be made from any known material that is hydrophobic, i.e. which does not absorb water vapour or water, and with a structure that allows transport of water vapour and water through the distance layer 20. For example; any hydrophobic polymer such as, polypropylene, polyethylene, poly-lactic-acid polymer, Nylon, hydrophobic fibers, hydrophobic foam; or any hydrophobic solid inert structure.

Figure 5:
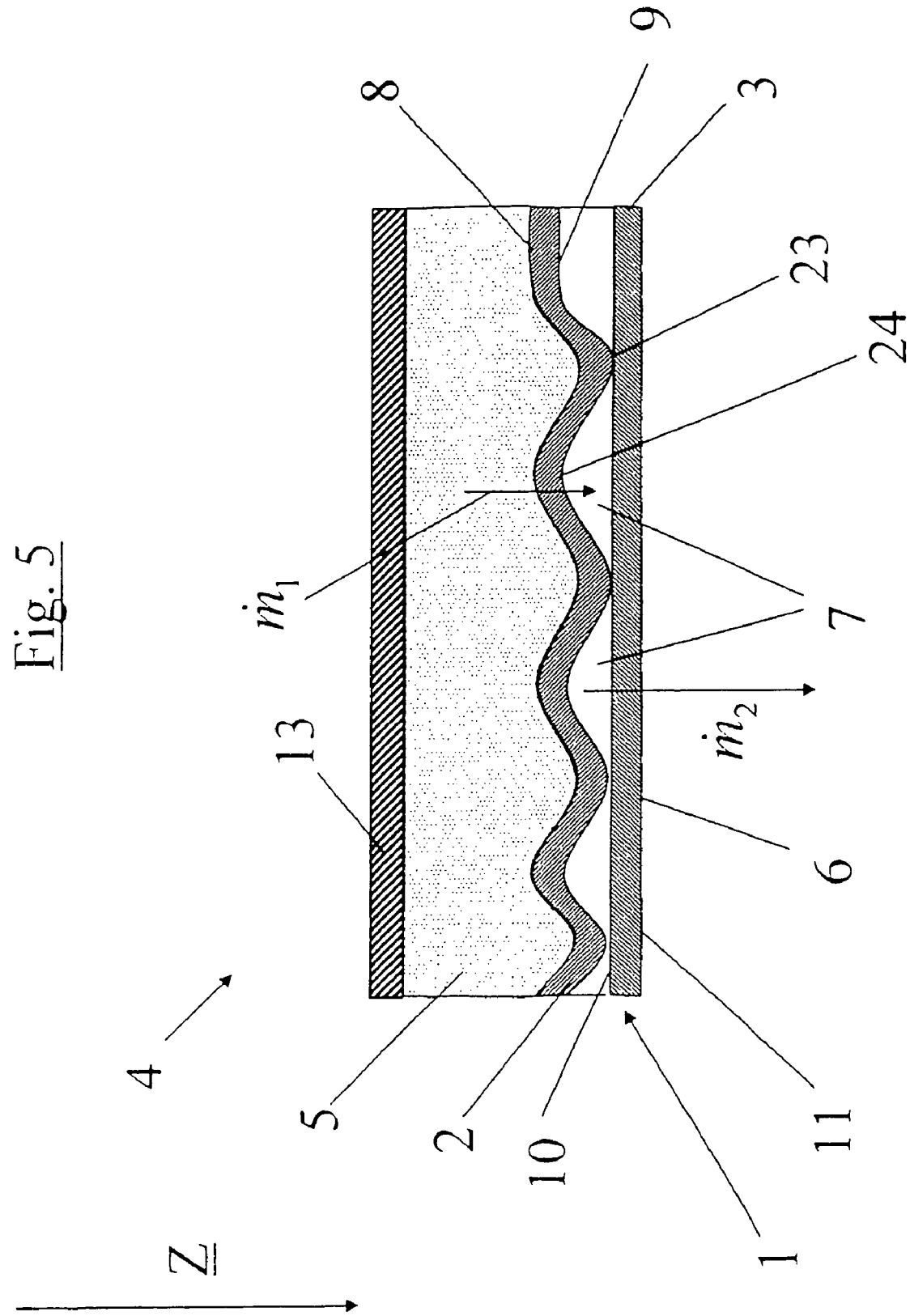
FIG. 5 schematically shows a cross-section view taken in the cross-section A-A in FIG. 1, according to a fourth embodiment of the present invention, and where.

FIG. 5 schematically shows a cross-section view in the cross-section A-A in FIG. 1, according to a fourth embodiment of the present invention. The first layer 2 is made profiled and has a three dimensional form with raised portions 23 and depressions 24. The first layer 2 is in contact with the second layer 3 at the apex of each of the raised portions 23. The raised portions 23 have the function of hydrophobic distance elements such that the space between the second layer 3 and the depressions 24 form the condensation zone 7. FIG. 5 also shows that the absorbent body 5 follows the contour of the first layer 2. The absorbent body 5 thus fills out all the depressions on the absorbent body facing side of the first layer 2. Those depressions are a consequence of the raised portions 23 on the second layer 3 facing side of the first layer 2.

Figure 6:
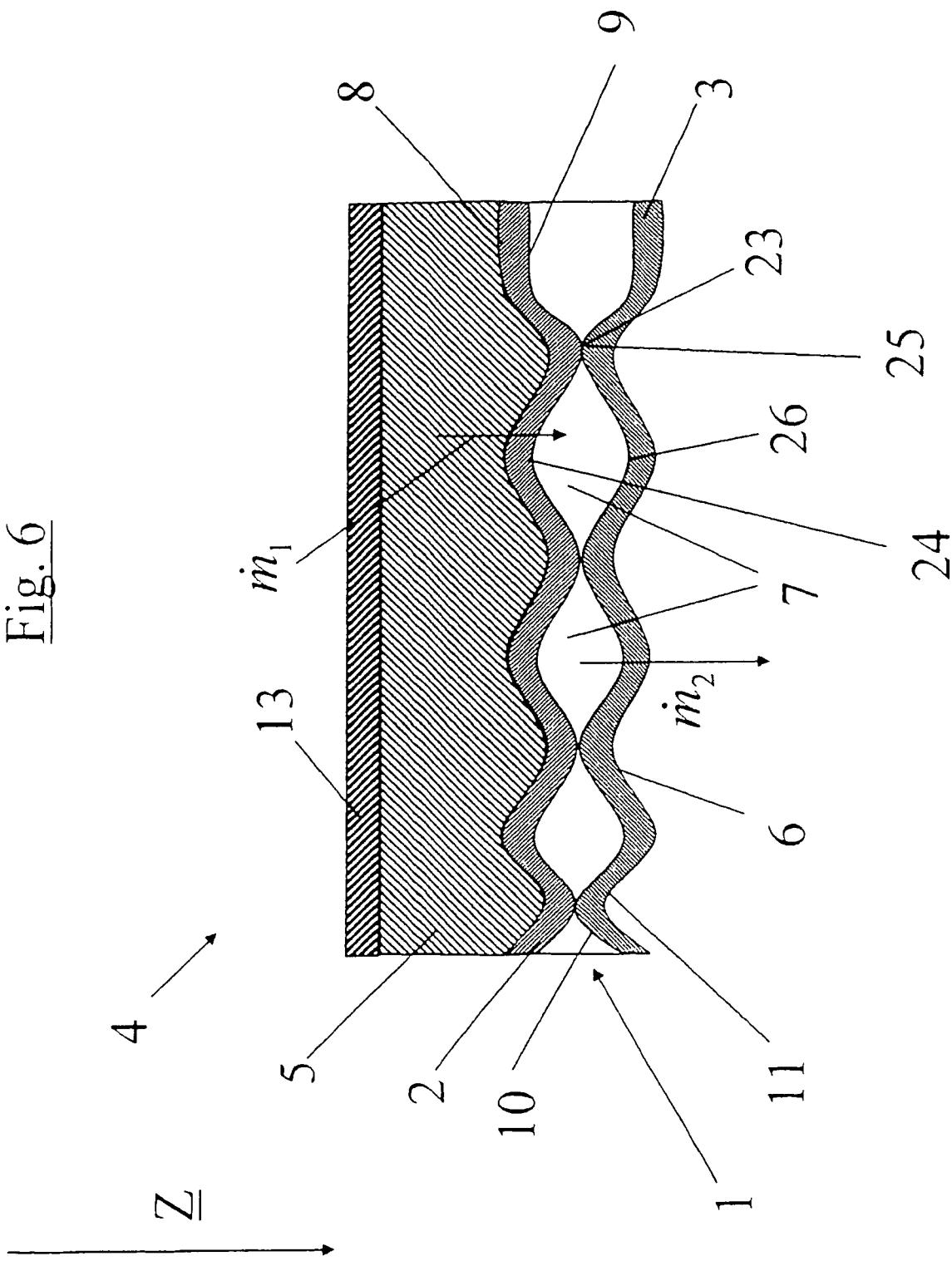
FIG. 6 schematically shows a cross-section view taken in the cross-section A-A in FIG. 1, according to a fifth embodiment of the present invention.

FIG. 6 schematically shows a cross-section view in the cross-section A-A in FIG. 1, according to a fifth embodiment of the present invention. The first layer 2 and the second layer 3 are made profiled such that the first and second layers 2, 3 are in contact in several points, and where the condensation zone 7 is created in the space between the profiled parts of the first and second layer 2, 3. In FIG. 6 the first layer 2 has the same topographical feature as in FIG. 5, i.e. with raised portions 23 and depressions 24. The second layer 3 has a corresponding topographical feature as the first layer 2, with raised portions 25 and depressions 26. The raised portions 23 of the first layer 2 are in contact with the raised portions 25 of the second layer 3. The raised portions 23, 25 of the first and second layers 2, 3 have the function of hydrophobic distance elements such that the space between the depressions 24 of the first layer 2 and the depressions 26 of the second layer form the condensation zone 7.

The invention is not limited to the above embodiments, but may be varied within the scope of the appended claims. For example, the distance element may be formed by any combination of the embodiments shown in FIGS. 3-6, i.e. for example an embossed first layer 2 according to FIG. 5 and hydrophobic particles 12 according to FIG. 3 placed in the space between the depressions 25 and the second layer 3.

The invention claimed is:

1. A breathable backsheet for an absorbent article, the backsheet comprising:
    a first layer adjacent to an absorbent body arranged in the absorbent article to face toward the user during use, said first layer being water vapor permeable and liquid impermeable;
    a second layer adjacent the first layer, said second layer being water vapor permeable and liquid impermeable;
    a condensation zone between the first layer and the second layer; and
    a three dimensional hydrophobic distance layer placed in the condensation zone creating a space between the first layer and the second layer, said distance layer comprising topographical features with raised portions and depressions on a first side of the distance layer and corresponding depressions and raised portions on a second side of the distance layer, the raised portions on the first side of the distance layer being in contact with the first layer, the raised portions of the second side of the distance layer being in contact with the second layer, and the raised portions creating a distance between the first layer and the second layer such that the space between the depressions and the layers creates the condensation zone,
wherein,
    the backsheet is water vapor permeable in a Z-direction from the absorbent body to the outside of the backsheet,
    the first layer is adapted to allow a first amount of mass flow water vapor ($m_1$) to pass through the first layer in the Z-direction, the second layer is adapted to allow a second amount of mass flow water vapor ($m_2$) to pass through the second layer in the Z-direction, $m_2$ is less than or equal to $m_1$, $m_1$ is a maximum 10,000 g/($m^2 \cdot 24$ hours) and $m_2$ is a maximum 2700 g/($m^2 \cdot 24$ hours) when the outside air has a relative humidity of about 90% and a temperature of about 23° C.,
    the condensation zone comprises an open volume between the first layer and the second layer and the minimum distance between the first layer and the second layer is 0.1 mm,
    the hydrophobic distance layer is arranged to condense water vapor within the condensation zone, and
    the condensation zone is adapted to temporarily condense and store an amount of water vapor ($t \cdot m_c$), where $m_c$ is the difference between $m_1$ and $m_2$, and t is the time period during which the condensed water vapor $m_c$ is stored, $m_2$ is less than a maximum amount of mass flow water vapor ($m_x$) allowed to pass through the second layer without forming any condensation of water vapor on the outside of the backsheet.

2. The breathable backsheet according claim 1, wherein the features of the backsheet are valid in an environment where the outside of the backsheet is uncovered and exposed to a room temperature of about 20° C.

3. The breathable backsheet according to claim 1, wherein the hydrophobic distance layer is in the form of a three dimensional net.

4. The breathable backsheet according to claim 1, further comprising a plurality of hydrophobic particles, the particles placed in the space between the depressions and the layers.

* * * * *